(12) United States Patent
Paul (10) Patent No.: US 7,766,941 B2
(45) Date of Patent: Aug. 3, 2010

(54) SPINAL SUPPORT, STABILIZATION (76) Inventor: Kamaljit S. Paul, 3220 Old Orchard La., Oshkosh, WI (US) 54901

( * ) Notice: Subject to any disclaimer, the term of this patent is extended or adjusted under 35 U.S.C. 154(b) by 1119 days.

(21) Appl. No.: 10/845,709

(22) Filed: May 14, 2004

(65) Prior Publication Data
US 2005/0261686 A1 Nov. 24, 2005

(51) Int. Cl.
A61B 17/70 (2006.01)
(52) U.S. Cl. .................................................. 606/257
(58) Field of Classification Search .................. 606/61; 285/146.1–146.3, 262–263
See application file for complete search history.

(56) References Cited

U.S. PATENT DOCUMENTS

| 2,062,985 | A | * | 12/1936 | Baticle | 14/18 |
| 2,776,697 | A | * | 1/1957 | Zerlaut | 72/466 |
| 3,858,578 | A | * | 1/1975 | Milo | 600/229 |
| 5,261,912 | A | | 11/1993 | Frigg | |
| 5,346,493 | A | | 9/1994 | Stahurski et al. | |
| 5,360,431 | A | | 11/1994 | Puno et al. | |
| 5,466,237 | A | | 11/1995 | Byrd, III et al. | |
| 5,476,465 | A | * | 12/1995 | Preissman | 606/279 |
| 5,540,688 | A | * | 7/1996 | Navas | 606/266 |
| 5,611,801 | A | | 3/1997 | Songer | |
| 5,624,442 | A | | 4/1997 | Mellinger et al. | |
| 5,649,925 | A | * | 7/1997 | Alacreu | 606/86 A |
| 5,662,653 | A | | 9/1997 | Songer et al. | |
| 5,669,910 | A | | 9/1997 | Korhonen et al. | |
| 5,683,390 | A | | 11/1997 | Metz-Stavenhagen et al. | |
| 5,713,898 | A | | 2/1998 | Stucker et al. | |
| 5,944,719 | A | * | 8/1999 | Leban | 606/59 |
| 6,090,111 | A | | 7/2000 | Nichols | |
| 6,123,708 | A | | 9/2000 | Kilpela et al. | |
| 6,241,730 | B1 | | 6/2001 | Alby | |
| 6,251,112 | B1 | | 6/2001 | Jackson | |
| 6,290,700 | B1 | * | 9/2001 | Schmotzer | 606/263 |

(Continued)

OTHER PUBLICATIONS

Ogando, Joseph. "Fastening innovations speed spine surgery: To replace set screws in spinal implants, Surgical Dynamics devised a threadless fastener with a helical-dovetail locking feature." Design News. 2001 Cahners Business Information. 2 sheets.

(Continued)

Primary Examiner—Thomas C Barrett
Assistant Examiner—Nicholas Woodall
(74) Attorney, Agent, or Firm—Thomas D. Wilhelm; Wilheim Law, S.C.

(57) ABSTRACT

Spinal support assemblies, and methods of use, provide stabilization of the treated portion of the spine while accommodating limited, controlled angular movement of the treated portion of the spine, also while limiting transverse movement of the spine. Adapters, such as lamellar hooks and/or bone screws attach the spinal support assembly to support vertebrae. Reinforcing rods in the spinal support assemblies embody any of a variety of structures and configurations, all of which provide for support and force transfer while providing for limited and controlled levels of dynamic, ongoing bending of the rod. The reinforcing rod can bend to accommodate limited bending of the treated portion of the spine, as the subject bends the spine in normal activities. The reinforcing rod stabilizes the vertebrae against vertical and/or transverse lateral movement of the reinforcing rod, members of the reinforcing rod, and/or vertebrae.

35 Claims, 5 Drawing Sheets

U.S. PATENT DOCUMENTS

| | | |
|---|---|---|
| 6,302,888 B1 | 10/2001 | Mellinger et al. |
| 6,478,797 B1 | 11/2002 | Paul |
| 6,523,624 B1 * | 2/2003 | Cousins et al. .............. 175/386 |
| 6,554,831 B1 | 4/2003 | Rivard et al. |
| 6,986,771 B2 | 1/2006 | Paul et al. |
| 6,989,011 B2 | 1/2006 | Paul et al. |
| 7,137,985 B2 | 11/2006 | Jahng |
| 2002/0120272 A1 | 8/2002 | Yuan et al. |
| 2003/0191470 A1 | 10/2003 | Ritland |
| 2003/0220642 A1 | 11/2003 | Freudiger |
| 2003/0220643 A1 * | 11/2003 | Ferree .................. 606/61 |
| 2004/0002708 A1 | 1/2004 | Ritland |
| 2004/0049189 A1 | 3/2004 | Le Couedic et al. |
| 2004/0049190 A1 | 3/2004 | Biedermann et al. |
| 2004/0073215 A1 | 4/2004 | Carli |
| 2004/0172025 A1 | 9/2004 | Drewry et al. |
| 2004/0215192 A1 | 10/2004 | Justis et al. |
| 2004/0225289 A1 | 11/2004 | Biedermann et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2005/0010220 A1 * | 1/2005 | Casutt et al. .................. 606/61 |
| 2005/0065515 A1 | 3/2005 | Jahng |
| 2005/0065516 A1 | 3/2005 | Jahng |
| 2005/0096652 A1 | 5/2005 | Burton |
| 2005/0113927 A1 | 5/2005 | Malek |
| 2005/0124991 A1 | 6/2005 | Jahng |
| 2005/0131407 A1 * | 6/2005 | Sicvol et al. .................. 606/61 |
| 2005/0143737 A1 | 6/2005 | Pafford et al. |
| 2005/0149020 A1 | 7/2005 | Jahng |
| 2005/0177157 A1 | 8/2005 | Jahng |
| 2005/0203513 A1 | 9/2005 | Jahng et al. |
| 2005/0203514 A1 | 9/2005 | Jahng et al. |
| 2005/0203517 A1 | 9/2005 | Jahng et al. |
| 2005/0203518 A1 | 9/2005 | Biedermann et al. |
| 2006/0041259 A1 | 2/2006 | Paul et al. |
| 2006/0195093 A1 | 8/2006 | Jahng |
| 2007/0055247 A1 | 3/2007 | Jahng |

OTHER PUBLICATIONS

"PWB Lumbosacral System." 1992 Cross Medical. Product literature. 6 sheets.

"Spiral Radius 90D™ Product Demonstration." 2000 Surgical Dynamics. 16 sheets.

"The Market for Spinal Implants." Located on the internet at http://www.crossmedical.com/spinal.html. 4 sheets.

\* cited by examiner

SPINAL SUPPORT, STABILIZATION

BACKGROUND

Spinal fixation devices are used to stabilize vertebrae in need of stabilization. For example, surgically fused vertebrae can benefit from such stabilization. Conventional devices, known for use in the lumbar region of the spine, generally employ spinal support assemblies. Such spinal support assemblies typically include a reinforcing rod, and an attachment adapter assembly. A typical attachment adapter assembly includes an adapter which extends generally between the reinforcing rod and a vertebra which provides a supporting foundation from which the vertebra or vertebrae being treated can be supported. A typical such spinal support assembly commonly employs two or more adapter assemblies, which support the spinal support assembly from two or more such foundation support vertebrae.

The adapter can include a lamellar hook which can be used to secure the adapter to a such support vertebra. In the alternative, the adapter assembly can include one or more e.g. titanium bone screws as elements separate and distinct from the adapter, itself, or loosely mounted to the adapter. The bone screws are used to secure the adapter to the support vertebra or vertebrae.

A typical reinforcing rod is a titanium rod having a nominal diameter of about 6 mm, and length sufficient to extend along the vertebrae being fused, and at least to the next adjacent vertebrae which can be used as the foundation support vertebrae. Such length provides sufficient purchase on the rod, by the adapter assemblies, to enable the surgeon to securely attach the adapters to the reinforcing rod, as well as to the support vertebrae. The rod diameter can, of course, be specified greater or less than the above-noted 6 mm as an adaptation to the general size and strength needs associated with the particular subject being treated. Such size and strength needs can vary according to the size of the subject or spine, or can vary according to the species being treated in the case of treatment of e.g. non-human subjects.

Attachment of the adapter/rod combination to adjacent vertebrae, e.g. foundation support vertebrae, by means of the adapters, and which support vertebrae are adjacent the vertebrae being treated and/or supported, and which provide the basis for supporting the rod, is known. Especially useful attachment combinations, namely reinforcing rod, adapter, and securing device, e.g. bone screw or hook, are taught in my U.S. Pat. No. 6,478,797, the disclosure of which is hereby incorporated herein by reference in its entirety.

The purpose of a spinal support assembly is to provide support to vertebrae which are being treated, typically vertebrae which are being fused to each other. However, in providing such support to the vertebrae which are being fused, such support is inherently a transfer of forces to and from the adjacent foundation, support vertebrae, by the spinal support assemblies, whereby at least some of the forces, which would normally be imposed on the vertebrae being treated, by-pass those treated vertebrae through the spinal support assembly.

For example, the forces which by-pass the vertebrae being treated can be characterizable as both vertical support loads and angularly-directed lateral loads.

Restated, the purpose of the spinal support assembly is to provide control of forces which would otherwise be applied to the vertebrae being treated. Further, a purpose is to serve as a force by-pass route once the spinal support assembly has been surgically attached to the support vertebrae. Movement of that portion of the spine to which the spinal support assembly is attached is effectively controlled by the inherent stiffness and rigidity of the reinforcing rod in combination with the stiffness and rigidity of the associated attachments, and any capacity for movement at the respective interfaces internal to the spinal support assembly, and between the spinal support assembly and the foundation support vertebrae. In known spinal support assemblies, the treated portion of the spine is effectively immobilized by the above-exemplified stiffnesses and rigidities.

The objective sought to be achieved by the surgical procedure wherein the forces are re-routed through the spinal support assembly, rather than accepting passage of such forces through the vertebrae being treated, is to neutralize or attenuate pain and dysfunction which is otherwise associated with the vertebrae which are to be fused. Such pain can be associated with neurocompression and/or with pain associated with loading and/or moving pain-generating tissues such as associated discs, facet joints, ligaments, muscles, or fracture fragments.

A problem associated with spinal support assemblies known in the art is that pain relief achieved by installing the spinal support assembly is achieved at the cost of effectively immobilizing that portion of the spine; namely immobilizing that portion of the spine both vertically and laterally. Such immobilizing of the spine correspondingly limits mobility of the patient. In addition, such immobilizing of the spine limits the ability of the associated foundation support vertebrae to adjust to the imposition of the forces so transferred, whereby the foundation support vertebrae can, over time, suffer accelerated degradation of their own capabilities.

The applicant herein contemplates that, in some instances, the need for stabilization of the respective vertebrae being treated does not necessarily correspond with a need for the affected components of the spine to be completely immobilized. Rather, in such instances, maintaining at least lateral mobility of the portion of the spine which is being treated can provide benefit to the subject being treated, greater than if the spine were conventionally immobilized against all movement. Namely, the subject retains at least some mobility of the fused portion of the spine.

In addition to improved mobility of the subject being treated, mobility of the affected portion of the spine enables the foundation support vertebrae to better adjust, in real time, to the dynamics of the forces being imposed on that portion of the spine. Such real-time adjustment to such forces, by the foundation support vertebrae, enhances prospects for the foundation support vertebrae to provide normal levels of vertebral support to the subject for normal life-cycle periods of time.

There is therefore a need for spinal stabilization apparatus which accommodates limited and controlled motion of the treated portion of the spine, while providing the required level of stabilization of the treated portion of the spine to support the dynamics of body forces being imposed on that portion of the spine by the subject's/patient's body, all in the context of controlling, limiting, the spatial volume of material which is being attached to the spine.

There is a corresponding need for spinal stabilization apparatus which accommodates limited lateral or angular movement of the treated portion of the spine while stabilizing the treated portion of the spine against transverse lateral movement and limiting the extent of vertical movement of the treated portion of the spine.

There is a corresponding need for spinal stabilization apparatus which accommodates limited and controlled motion of the treated portion of the spine while providing the required level of stabilization of the treated portion of the spine, all in the context of minimizing the amount of space which is occupied by such spinal support apparatus.

Specifically, there is a need for spinal stabilization apparatus which accommodates limited lateral angular movement of the treated portion of the spine while stabilizing the treated portion of the spine against transverse lateral movement, and limiting the extent of vertical movement of the treated portion of the spine.

There is a yet further need to provide such spinal stabilization apparatus in a format and structure which follows closely the known configuration of a single reinforcing rod supported by first and second adapter assemblies, wherein the adapter assemblies provide the interface between the reinforcing rod and the foundation support structure.

SUMMARY

This invention provides spinal support assemblies, and methods of use, which provide a required level of stabilization of the treated portion of the spine while also accommodating limited and controlled angular movement of the treated portion of the spine, also while limiting transverse lateral movement of the treated portion of the spine. The invention can include known technology to attach the spinal support assembly to support vertebrae. Namely, the spinal support assembly can include conventional adapters. The attachment to the spine can be e.g. through lamellar hooks, and/or through bone screws which are screwed into the foundation support vertebrae. Substantial novelty is provided in the structure of the reinforcing rod, itself.

While known technology rods are solid-shaft constructions, rods of the invention take on a variety of structures and configurations, all of which provide for the needed level of support and force transfer while also providing for a limited and controlled level of angular movement, namely dynamic and ongoing bending of the rod, in response to forces exerted on the spine by e.g. the usual dynamic movements of the subject. Further, the reinforcing rods of the invention accommodate little or no transverse movement of elements of the rod with respect to each other. Namely, the reinforcing rod can bend in order to accommodate at least limited bending of the treated portion of the spine, e.g. the treated vertebrae and support vertebrae, as the subject elects to bend the spine in normal daily activities. But the reinforcing rod stabilizes the vertebrae against vertical and/or transverse lateral movement of the reinforcing rod, members of the reinforcing rod, and/or vertebrae.

The invention is not limited in its application to the details of construction or the arrangement of the components set forth in the following description or illustrated in the drawings. The invention is capable of other embodiments or of being practiced or carried out in other various ways. Also, it is to be understood that the terminology and phraseology employed herein is for purpose of description and illustration and should not be regarded as limiting. Like reference numerals are used to indicate like components.

DESCRIPTION OF THE ILLUSTRATED EMBODIMENTS

Figure 1:
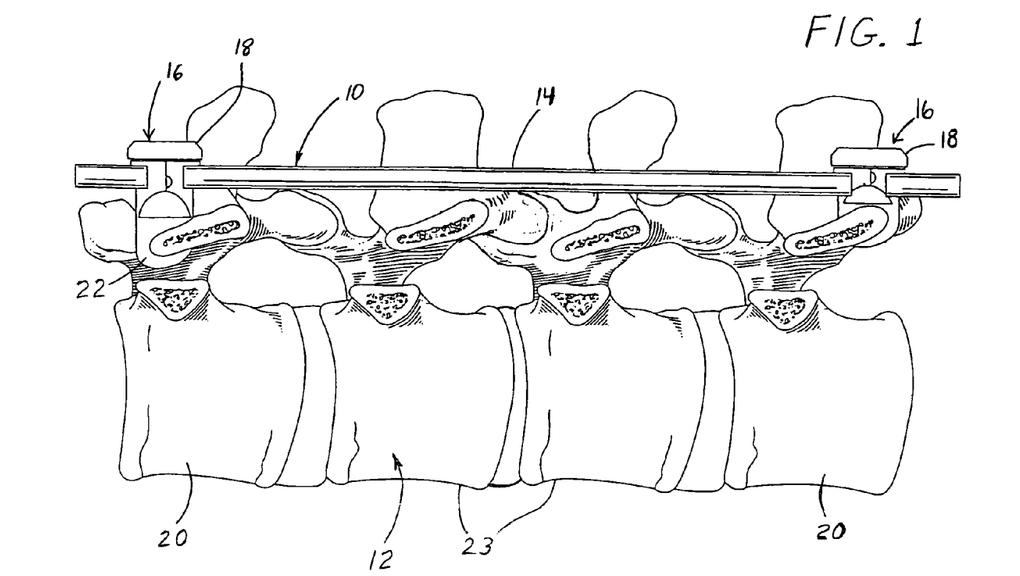
FIG. 1 shows a side elevation view, partially cut-away, of a supported section of a spine, including foundation support vertebrae, and vertebrae being treated, and a spinal support assembly of the invention supporting the spine.

FIG. 1 illustrates generally the use of spinal support assemblies 10 of the invention in cooperation with a spine 12 of a patient being treated. The spinal support assembly includes a reinforcing rod 14, shown generically in FIG. 1, and first and second attachment adapter assemblies 16. Attachment adapter assembly 16 includes an adapter 18 which extends generally between reinforcing rod 14 and a supporting vertebra 20 of the spine being supported. Adapter 18 includes lamellar hook 22 which interfaces directly with the support vertebra, and serves to anchor the adapter to the vertebra. The result of such structure and anchoring is that the spinal support assembly is secured to first and second supporting vertebrae 20, on opposing ends of the collective length of vertebrae 23 which are being treated.

The attachment adapter assembly 16 illustrated is merely illustrative of a wide variety of constructions of adapter assemblies which can be used in spinal support assemblies of the invention. For example and without limitation, instead of employing a lamellar hook, the adapter assembly can be anchored to the respective support vertebra by one or more bone screws which extend through the attachment adapter and into the underlying vertebra, whereby the attachment adapter is secured to the supporting vertebra by the bone screw(s) rather than by a lamellar hook.

Figure 2:
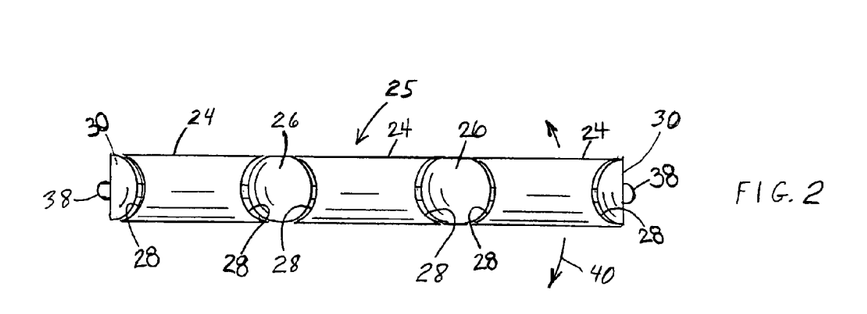
FIG. 2 shows a side elevation view of a first embodiment of reinforcing rod assemblies useful in spinal support assemblies of the invention.
Figure 3:
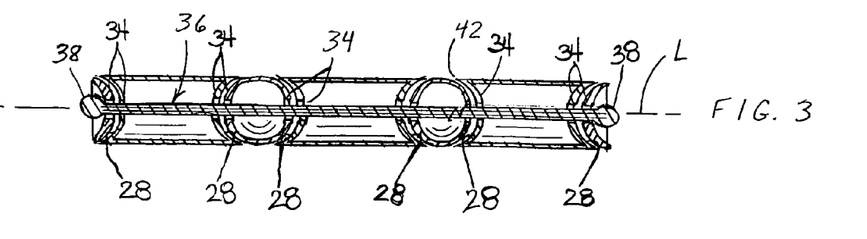
FIG. 3 shows a longitudinal cross-section of the reinforcing rod assembly of FIG. 2.

FIGS. 2-17 illustrate multiple embodiments of structures of novel reinforcing rods, and reinforcing rod assemblies, of the invention which can be used in spinal support assemblies of the invention. FIGS. 2 and 3 illustrate a first embodiment of such inventive reinforcing rod assemblies. The embodiment of FIGS. 2 and 3 comprises a plurality of elongate rod elements 24, joined in end-to-end relationship with respect to each other in a rod assembly 25, with generally spherically-shaped joint balls 26 disposed between the respective elongate rod elements 24. Each elongate rod element has first and second recessed ends 28 which are adapted and configured to receive the respective joint balls 26.

Three rod elements 24 are illustrated, with two joint balls 26 between the three elongate rod elements. First and second end caps 30 are located on opposing ends of distal ones of the elongate rod elements. End caps 30 fit into the respective recessed ends 28 of the corresponding rod elements.

Elongate rod elements 24, joint balls 26, and end caps 30 all have generally centrally located apertures 34 which, in the assembled reinforcing rod assembly 25, are generally aligned with each other along the length of the reinforcing rod assembly, at a longitudinal axis "L" of the rod. A cable 36 extends in a generally straight line along a path through the aligned apertures 34, and is terminated on opposing ends of the rod assembly such as by knob-shaped enlargements such as welds 38. Prior to termination, cable 36 is placed under tensile stress, thus pre-tensioning the cable prior to creating welds 38, such that the retraction forces in the cable, in combination with the enlarged ends on the welded cable, maintain the tension on the cable and thus apply a stress on the various members of the rod assembly and thereby draw the various members of the rod assembly, in compression, toward each other, whereby the elements of the reinforcing rod assembly are held together by the pre-tensioned cable. As a result, the elements of the rod assembly 25 are drawn toward each other along the length of the cable, whereby compressive forces are maintained between the respective members of the rod assembly by cable 36.

Given the end-to-end assembly configuration of the elongate rod elements and the joint balls to each other; given the tension in cable 36, the cable forces the facing surfaces of the joint balls and elongate rod elements into frictional relationships with each other, whereby the elongate rod elements can move angularly with respect to each other, at the joint ball interfaces. Thus, while all of the rod assemblies illustrated herein are shown in straight-line arrangement, the respective elongate rod elements 24 can move in angular directions as suggested by arrows 40 in e.g. FIG. 2. The sizes of the openings at apertures 34 are sized generally to the diameter of cable 36 such that rod elements 24, joint balls 26, and end caps 30 are generally prevented from moving transversely with respect to the cable, and with respect to each other.

Angular limits of the degree to movement between a respective elongate rod element and an associated joint ball can be controlled by providing e.g. angular stop projections (not shown) on the respective joint ball. When such stop projection is present, the stop is located on the joint ball such that the distal edge 42 at the respective end 28 of the elongate rod element abuts the stop when the maximum angle of movement has been reached by the respective elongate rod element 24 relative to the respective joint ball.

The amount of lateral force required to bend the rod assembly, namely to cause angular movement of the rod assembly, in part depends on the amount of tensile stress being placed on the cable, and thus on the amount of frictional force being applied on the respective elongate rod elements and joint balls at the interfaces between these respective members of the reinforcing rod assembly. As the tension on cable 36 increases, the amount of force required to change the angle of extension, of one rod member with respect to another rod member, increases.

Thus, magnitude of the tension on the cable defines the magnitude of the element-to-element frictional engagement between the respective rod elements, and thus the magnitude of force required to angularly displace one rod element relative to another rod element, thus to bend the rod assembly. Accordingly, the magnitude of the tension on the cable, and thus the compression forces drawing the facing ends of adjacent ones of the rod elements toward each other, establishes the friction-related resistance to angular movement of adjacent cable ends relative to each other and thereby determines the amount of force required to effectuate such friction-limited angular/bending movement of the rod elements relative to each other.

If desired, a lever-type end cap can be applied to pre-tensioned cable 36 at the time the rod assembly is assembled whereby the using surgeon, who receives the rod assembly with the cable in the pre-tensioned condition, can further tension the cable as desired before installing the rod assembly in the patient, in order to increase the forces at the interfaces between the rod elements and the balls, thereby increasing the force which is needed to move a first member of the rod assembly, in an angular direction, with respect to a second different member of the rod assembly.

While elongate rod elements 24 have been shown as elongate rod members, and joint balls 26 have been shown as spherical structures, a wide variety of lengths of both rod elements 24 and joint balls 26 can be employed at will. For example, rod elements 24 can be foreshortened as desired, so long as the ends thereof are not subsumed within each other so much as to preclude the longitudinal extension of the rod through the rod elements while suitably limiting the size of the corresponding apertures 34. Similarly, balls 26 can be elongate if desired, so long as they provide, in combination with the rod elements, for the disclosed articulation of the rod members with respect to each other such as at arrows 40. Similarly, while elongate rod elements 24 and joint balls 26 are shown with generally spherically-shaped surfaces, male and female, such facing surfaces can have a wide variety of complementary shapes and/or configurations so long as the rod elements 24 and joint balls can be effectively angularly articulated with respect to each other when a transverse force is applied to the reinforcing rod assembly.

Figure 4:
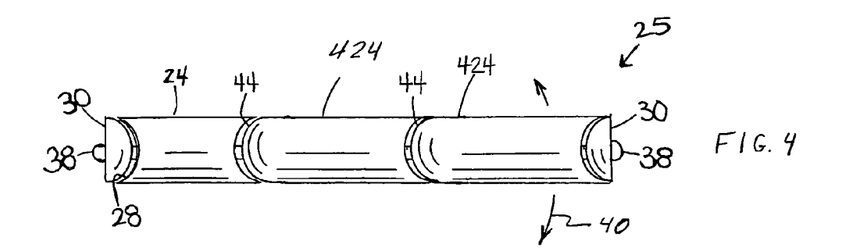
FIG. 4 shows a side elevation view of a second embodiment of reinforcing rod assemblies useful in spinal support assemblies of the invention.
Figure 5:
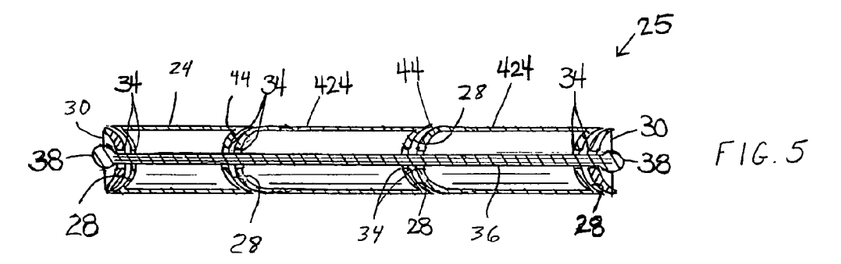
FIG. 5 shows a longitudinal cross-section of the reinforcing rod assembly of FIG. 4.

FIGS. 4 and 5 illustrate a second family of embodiments of rod assemblies 25 of the invention, this second family of embodiments being closely related to the embodiments of FIGS. 2-3. The difference in the embodiments of FIGS. 4-5 is that the structure and function of the joint balls of FIGS. 2-3 have been subsumed into modified structures of the elongate rod elements 424 of the embodiments of FIGS. 4-5. Accordingly, in the embodiments of FIGS. 4-5, the elongate rod elements 424 are articulated directly with respect to each other, without any intervening joint balls. The same end caps 30 are shown being used. The same cable 36 extends through apertures 34 in the respective elongate rod elements and end caps. The end one 24 of the elongate rod elements has two concave ends 28 as in the embodiments of FIGS. 2-3. The modified elongate rod elements 424 have a first concave end 28 and a second convex end 44. Except for the ends of the rod assembly, facing ones of the convex and concave ends directly interface with each other, so as to accommodate the above discussed angular motion with respect to each other. Such angular motion is, as in FIG. 3, suggested by arrows 40 in FIG. 4.

It is seen that the embodiments of FIGS. 4-5 use a smaller number of parts than the embodiments of FIGS. 2-3. However, the assembly in FIGS. 2-3 is symmetric with respect to length of the rod assembly, whereas the assembly of FIGS. 4-5 is asymmetric in terms of the piece parts used in the rod assembly.

If desired, end caps 30 can be incorporated into either or both of elongate rod elements 24 or 424, thereby reducing even further the number of piece parts which are assembled in making a such reinforcing rod assembly.

Figure 6:
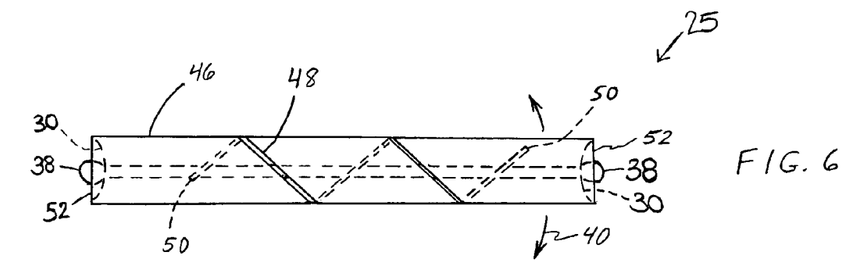
FIG. 6 shows a side elevation view of a third embodiment of reinforcing rod assemblies useful in spinal support assemblies of the invention.
Figure 7:
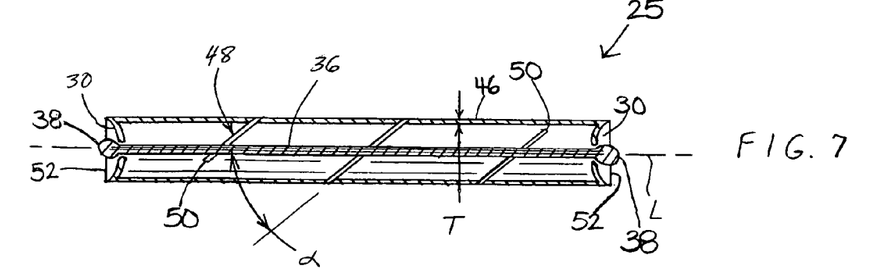
FIG. 7 shows a longitudinal cross-section of the reinforcing rod assembly of FIG. 6.

FIGS. 6-7 illustrate a third family of embodiments of reinforcing rod assemblies of the invention. The embodiments of FIGS. 6-7 are somewhat related to the embodiments of FIGS. 2-5, but with significant differences. The embodiments of FIGS. 6-7 are related to the embodiments of FIGS. 2-5 in that there is a longitudinally-extending outer perimeter, and a tensioned cable extending along the longitudinal axis of the reinforcing rod assembly.

Specifically, in the embodiments of FIGS. 6-7, reinforcing rod assembly 25 comprises a longitudinally-extending hollow cylindrical body 46 which in general defines the length of the reinforcing rod. Cylindrical body 46 has end caps 30. Cylindrical body 46 has an inner surface and an outer surface, and a thickness "T" between the inner and outer surfaces. Magnitude of thickness "T" is typically uniform along the length of the cylindrical body. End caps 30 can be integral with the cylindrical body as shown, or can be separate piece parts which are effectively secured to, or otherwise joined with, the cylindrical body. A tensioned cable 36 extends along the length of the cylindrical body and interacts with the cylindrical body through end caps 30.

A flex feature 48 extends along the length of the cylindrical body, and extends about the circumference of the cylindrical body. In the illustrated embodiment, flex feature 48 is exemplified by a spiral-shaped cut which extends about the circumference and along the length of the cylindrical body. In the illustrated embodiment, the spiral-shaped cut extends along less than all of the length of cylindrical body 46, namely extends along that portion of the length of the cylindrical body over which the user desires a flex characteristic which enables flexing of the cylindrical body to a degree greater than the flexure characteristic which is inherent in the structure and composition of the cylindrical body. Further, the spiral-shaped cut has first and second ends 50 which are spaced from opposing ends 52 of the cylindrical body.

In many cases of the embodiments of FIGS. 6-7, angle α of the spiral cut with respect to longitudinal axis "L" is constant over the length of the spiral cut. Assuming constant flexure characteristics in the material and structure of the cylindrical body absent the spiral cut, and where the angle α is constant, the lateral force required to achieve a given degree of flexing of the rod assembly at a given point along the length of the rod assembly is generally consistent over the length of the spiral cut.

In some instances, the angle α of the spiral cut varies along the length of the cylindrical body. In such instances, and again assuming constant flexure characteristics in the uncut material and structure of the cylindrical body, the flexure characteristics of the cylindrical body vary according to the variations in angle α.

In the embodiments illustrated in FIGS. 6-7, the flex feature cut is represented by an incision made by a sharp instrument, without the removal of any substantial amount of material from the locus of the cut. In such structure, the side walls of the cut are in facing relationship with each other, and are generally in surface-to-surface contact with each other.

Thus, when a transverse force is imposed on the cylindrical body of a rod assembly of FIGS. 6-7, the uncut ends of the cylindrical body respond in accord with the structural features of the uncut cylindrical body. The spiral cut portion of the cylindrical body responds generally in accord with the structural features of the uncut cylindrical body, but with the facing surfaces of the cut exerting sliding forces against each other, and sliding with respect to each other. The resulting flex characteristics of the cylindrical body thus accommodate greater degrees of flex per length of the cylindrical body over the length of the cylindrical body which is characterized by the spiral cut than over the portions of the length of the cylindrical body which have not been cut. Thus, in the illustrated embodiment, the cut central portion of the cylindrical body flexes to a greater extent, per unit length of the cylindrical body, than the uncut end portions of the cylindrical body.

The spiral cut can extend over a portion, but less than all, of the length of the cylindrical body, as shown. As desired, the spiral cut can extend over the entirety of the length of the cylindrical body. The spiral cut can be intermittent along the length of the cylindrical body, thereby resulting in multiple spiral cuts, but with only one such cut being active at any point along the length of the cylindrical body. Further, flex feature 48 can be embodied in multiple spiral cuts at any given point along the length of the cylindrical body. Such multiple spiral cuts are spaced from each other about the circumference of the cylindrical body.

Angle α can be any angle, greater than zero, with respect to the longitudinal axis, up to and including 90 degrees. Typically, angle α is between about 10 degrees and about 80 degrees, and is most typically between about 35 degrees and about 60 degrees, with respect to the longitudinal axis.

Choosing to not be bound by theory, applicant contemplates that the incremental increase in flexing which can be attributed to the cut is a result of the side walls of the cut sliding radially with respect to each other, or otherwise flexing out of the surface of the cylindrical body, as a lateral force is exerted on the cylindrical body.

Where the magnitude of angle α exceeds about 60 degrees to about 75 degrees, the cut generally extends about less than 360 degrees of the circumference of the cylindrical body. In such cases, the flex feature typically comprises multiple cuts, and each cut generally extends about only a portion of the cylindrical body, such as up to about 270 degrees about the circumference, typically up to about 180 degrees about the cylindrical body.

One or more of the multiple cuts, e.g. all of the multiple cuts, can each be represented by a plurality of cut elements arranged in a line. Namely, a given cut can be represented by a series of spaced cuts, which can be generally characterized as a line of perforations.

In such line of perforations, each such cut can be elongate, along the length of the line of perforations, or can be circular, such as a perforation made by a puncturing pin point or punch.

Any such cut, whether a continuous line, or an intermittently-expressed line of perforations, or a series of intermittent lines which are not readily characterized as lines of perforations, can be expressed through less than the entirety of the thickness "T" of the cylindrical body. Such cuts appear more as a line of one or more depressions, in any of the linear arrangements discussed herein, wherein the depths of such depressions extend from the outer surface, from the inner surface, or both, of the cylindrical body.

The invention further contemplates that flex feature 48 can include one or more cuts wherein a small amount of material is removed from the location of the cut so as to space the facing walls of the cut from each other, as illustrated in FIGS. 6 and 7. In such embodiments, the space between the facing walls of the cut further influences the ability of the cylindrical body to resist flexing forces. A first increment of increase in flex rate per unit of applied force is attributable to the discontinuity of the material of the cylindrical body at the location of the cut, whereby the material of the facing walls of the cut can respond more individually to the forces than if the cut did not exist. A second increment of increase in flex rate per unit of applied force is attributable to any distance between the facing side walls of the cut. Namely, as the cylindrical body flexes, the facing side walls of any cut, toward which the cylindrical body flexes, are brought closer together. To the extent the flexure is sufficiently great to bring the facing side walls into e.g. abutting contact with each other, such contact resists further flexure of the cylindrical body, thus to provide a step increase in the flexing resistance.

Considering the flexure properties which are desired of cylindrical body 46; considering the benefits of effecting abutment of the facing side walls of the cut against each other, thickness "T" of the side walls of the cylindrical body is typically on the order of about 0.4 mm to about 2 mm, more typically about 0.8 mm to about 1.5 mm. In light of such thickness parameters, and given the desired corresponding uncut flexural properties of the cylindrical body, material for the cylindrical body is typically selected from among the known plastics which are known to be safe for use in the living, e.g. human or animal, body.

As in the embodiments of FIGS. 2-5, in the embodiments of FIGS. 6-7, the diameter and tension of cable 36 have significant affects on the underlying flexing properties of the reinforcing rod assembly 25. Generally, increased tension, and increased diameter of the cable, as well as increased thickness "T" of the cylindrical body, each and collectively, affects an increase in resistance of the reinforcing rod assembly, to flexing.

So long as the diameter of cable 36 is small relative to the diameter of cylindrical body 46, any contribution of cable 36 to flex resistance is nominal. However, in a family of such reinforcing rod assemblies wherein the diameter of cable 36 is a variable, increases in diameter of cable 36 are accompanied by an increased contribution of the cable 36 to the flexure resistance of the reinforcing rod assembly 25.

Figure 8:
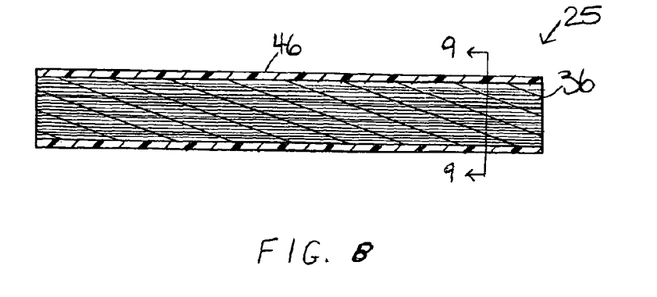
FIG. 8 shows a side elevation view, with parts cut away, of a fourth embodiment of reinforcing rod assemblies of the invention.
Figure 9:
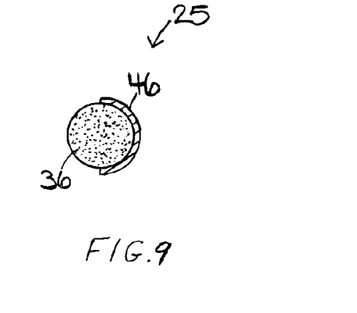
FIG. 9 shows a transverse cross-section of the reinforcing rod assembly of FIG. 8.

FIGS. 8 and 9 illustrate an extension of the structures of the reinforcing rod assemblies illustrated in FIGS. 6-7. Both FIGS. 8 and 9 show a reinforcing rod assembly wherein a cable 36 is generally enclosed within a cylindrical body 46, and wherein the diameter of the cable 36 generally fills the cylindrical body. FIG. 8 shows the cylindrical body cut-away from the front portion of the reinforcing rod assembly, whereby the cross-section view of FIG. 9 shows the cylindrical body encompassing only half of the circumference of the cable. In this embodiment, in the un-cut-away article, the cylindrical body generally encompasses the full circumference of the cable.

In the embodiments of FIGS. 8-9, with the diameter of the cable greatly increased as compared to the cable shown in FIGS. 6-7, the contribution of the cable to overall flex resistance of the reinforcing rod assembly is a substantially greater fraction of the overall flex resistance than in the embodiments of FIGS. 6-7. At the same time, and assuming use of the same material composition, and a common thickness "T" for the cylindrical body, the fractional contribution of the cylindrical body to overall flex resistance is correspondingly less. Since the contribution of the cylindrical body is correspondingly less, the configuration and/or structure and/or composition of the cylindrical body is of less significance to the overall flexural performance of the reinforcing rod assembly.

Within the above context, the flex feature 48, such as a cut, may or may not be present. Even if the flex feature is present, the affect of the flex feature on overall flexing properties of the reinforcing rod assembly is diminished to the extent of the control of flex properties, which is being exerted by cable 36. In that regard, the material and structural properties of cylindrical body 46 similarly matter less in this embodiment, again because the degree of control of overall flexural properties which is inherent in the larger diameter of cable 36 is so much greater than the contribution of the cylindrical body that the contribution of the cylindrical body is generally nominal by comparison.

Indeed, the design and configuration of cable 36 can be selected such that the flexural properties of cable 36 are generally sufficient to provide the desired level of flexing and flexural resistance, to the reinforcing rod assembly. In such instance, the material and structure of cylindrical body 46 can be selected for other than its mechanical strength and/or flexural properties. Rather, cylindrical body 46 can be specified so as to provide other desired properties such as serving as a shielding interface, shielding the soft tissues of the body, into which the spinal support assembly is installed, from the cable. So while the cylindrical body can, in the embodiments of FIGS. 8-9, include a flex feature 48, where the cable is the dominant provider of flexure control, such flex feature is typically not employed as a primary advantage in the cylindrical body in these embodiments.

Figure 10:
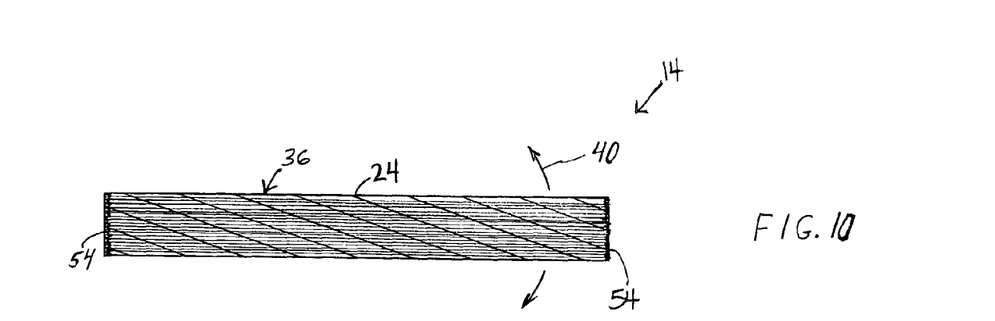
FIG. 10 shows a side elevation view of a fifth embodiment of reinforcing rod assemblies useful in spinal support assemblies of the invention.

FIG. 10 illustrates perhaps the simplest embodiment of reinforcing rods 14 useful in the invention. In FIG. 10, the reinforcing rod is shown as designed and configured to be used in a spinal support assembly 10. As in the embodiments of FIGS. 8-9, rod 24 is a stranded cable 36. The ends of the respective cable strands have been joined to each other such as by forming a weld 54 which joins the ends to each other, thereby to prevent any strand ends from separating from the bulk of the cable body.

In such embodiment, the joining of the strand ends to each other provides the effect of a cap on the end of the cable, which ties all the cable strands together. Such tying of the cable strands to each other avoids any of the cable strands straying from the general direction of extension of the cable.

Further to such embodiment, some or each of the cable strands can be coated with protective interface material which separates and shields the soft tissues of the body from the strength-providing material of the respective strands of the cable. Thus, where a metal cable strand is coated with a polymeric coating material, the polymeric coating material can function as a protective interface protecting soft body tissues from direct contact with the metal of the cable strand. Such protective coating can be applied to any or all of the strands of cable 36 in any of the embodiments which employ a stranded cable, along any or all portion or portions of the length of the cable. Further, a cylindrical body 46, not shown, which performs a shielding function can be applied to cable 36, or a non-stranded rod, in any of the embodiments of the invention.

Still referring to FIG. 10, the cap weld 54 extends only a nominal distance from the end of the cable, whereby the flexibility inherent in the unwelded portions of the length of the cable provide the dominant flex properties of the cable. Referring to FIG. 1, and considering the rod 14 to be the cable 36 disclosed in FIG. 10, any extension of cap weld 54 between adapters 18 can affect the flexural properties of rod 14/cable 36. Accordingly, in a spinal assembly 10, cap weld 54 typically does not extend along the length of cable 36 between the adapters 18.

Figure 11:
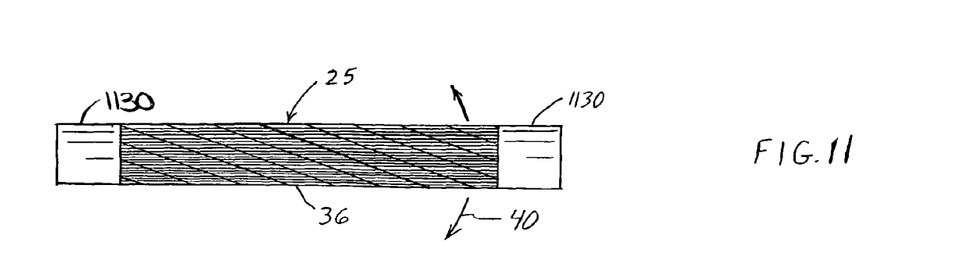
FIG. 11 shows a side elevation view of a sixth embodiment of reinforcing rod assemblies useful in spinal support assemblies of the invention.
Figure 12:
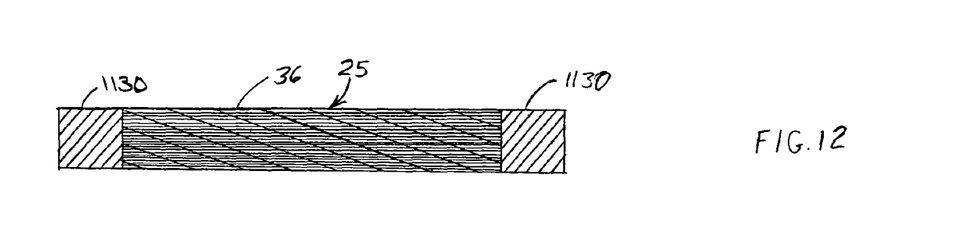
FIG. 12 shows a longitudinal cross-section of the reinforcing rod assembly of FIG. 11.

FIGS. 11 and 12 illustrate an embodiment of the rod assembly 25 wherein end caps 1130 are welded or are otherwise affixed to the ends of cable 36. In some embodiments, separate cap welds, not shown, are used in addition to the affixation of the end of the cable to the respective end cap 1130. In other embodiments, the affixation of the end of the cable to the respective end cap 1130 is used to additionally secure the ends of the cable strands to each other thus to prevent any strands from deviating from the general direction of extension of the cable.

As shown in cross-section in FIG. 12, the configuration of an end cap 1130 is that of a length of a solid rod whose cross-section approximates the diameter of cable 36, and is aligned with the length of the cable 36, whereby the diameter of the resulting rod assembly 25 is generally constant across the joints between the end caps 1130 and the ends of the cable.

End caps 1130 are displaced from each other by a distance which is compatible with the adapters 18 being attached to the rod assembly at end caps 1130. Accordingly, any transverse compressive force applied to the diameter of the rod assembly by the adapters, in mounting the adapters to the rod assembly, is received directly at the adapters, whereby the solid cross-sections of the end caps absorb such transverse compressive force with little if any of such compressive force being transferred to the cable body.

Figure 13:
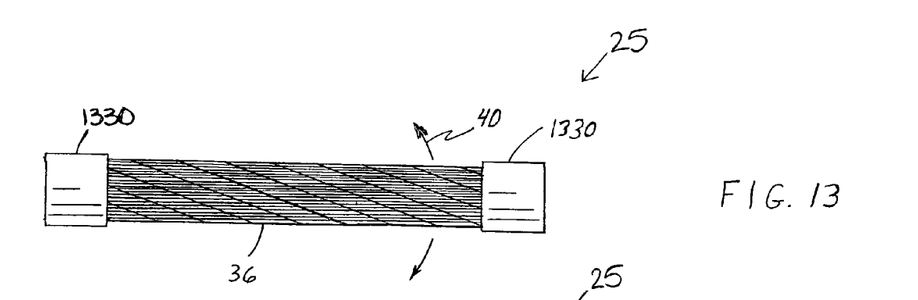
FIG. 13 shows a side elevation view of a seventh embodiment of reinforcing rod assemblies useful in spinal support assemblies of the invention.
Figure 14:
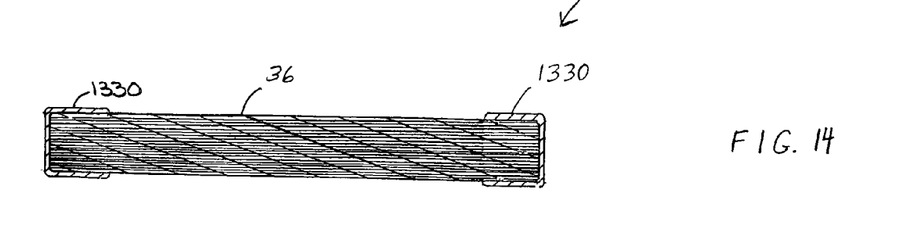
FIG. 14 shows a longitudinal cross-section of the reinforcing rod assembly of FIG. 13.

FIGS. 13-14 illustrate a family of embodiments of the invention wherein end caps 1330 extend over, and receive, the ends of cable 36. Such end caps are secured to the cable at such end locations by, e.g. welding the end caps to the cable. Such affixation can also be effected by, without limitation, chemical or thermal bonding, by mechanical crimping or other mechanical technique, or by any of a wide variety of other known methods for affixing materials to each other, so long as the resulting affixation is acceptable, e.g. medically safe, for use in the intended medical environment.

Still referring to FIGS. 13-14, a cylindrical body, not shown, such as that shown in FIGS. 6-9 can be employed in the embodiments of FIGS. 13-14, between end caps 1330. Where used, such cylindrical body is structured and configured such that the resulting diameter of the cable plus cylindrical body, between end caps 1330, is generally the same as the diameters of the end caps, whereby the rod assembly has a generally common diameter along the entirety of the length of the rod assembly.

Figure 15:
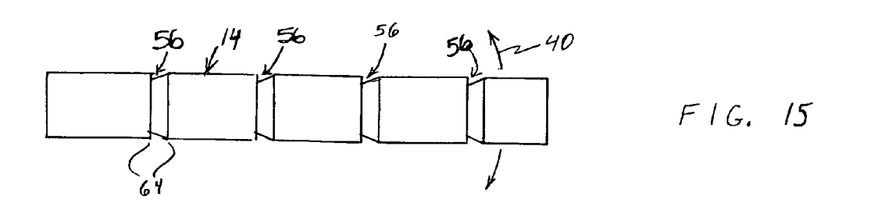
FIG. 15 shows a side elevation view of an eighth embodiment of reinforcing rod assemblies useful in spinal support assemblies of the invention.
Figure 16:
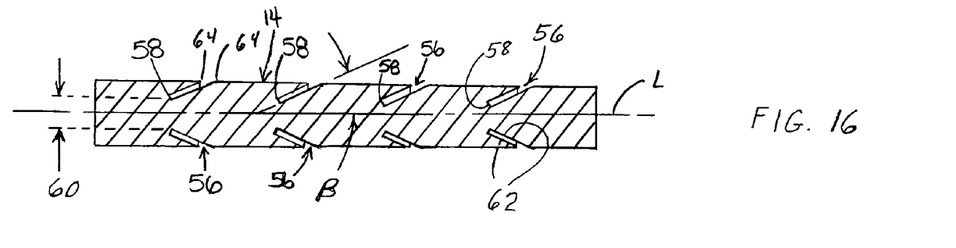
FIG. 16 shows a longitudinal cross-section of the reinforcing rod assembly of FIG. 15.

FIGS. 15-16 illustrate a reinforcing rod 14 which is made from a unitary body. Reinforcing rod 14 can be made, for example, by starting with a conventional e.g. 6 mm rod as is conventionally known for use in lumbar spinal support assemblies, and making certain modifications to such rod in order to provide the desired level of flexural properties in such rod. The modifications illustrated in FIGS. 15-16 are slits 56 which extend from the outer surface of the rod inwardly into the rod at an angle $\beta$ of about 10 degrees to about 90 degrees to the longitudinal axis "L". Slits 56 extend inwardly from the outer surface toward the longitudinal axis "L", to a dead end 58 of the slit, most remote from the outer surface, and leaving an uncut, unslit portion 60 of the diameter of the rod, between the dead end 58 and any slit feature positioned longitudinally-adjacent the respective end 58, and positioned transversely of the respective end 58. Such "any" slit feature can be an extension of the respective slit feature being examined. For example, where the slit extends entirely about the circumference of the rod, as in FIGS. 15 and 16, the uncut, unslit portion 60 of the rod illustrated in FIG. 16 represents a portion of the same slit 56, as viewed across the diameter of the rod.

The invention contemplates a large family of potential slit embodiments, both configurations of the slits themselves, and designs and configurations of the slits with respect to each other along the length of, and about the circumference of, the rod. For example, the invention contemplates a plurality of slits arrayed as an intermittent set of slits about the circumference of the rod, at a given location along the length of the rod, or at incremental changes along the length of the rod, such as in a spiral arrangement, or crossing spiral arrangements.

Whatever the structure of a given slit, whatever the configuration of any such slit array or arrays, each effective slit 56 has opposing side walls 62 which move toward each other, especially at the outer surface of the rod, as the rod is flexed toward the respective slit, namely in a plane which contains the longitudinal axis of the rod and which passes through the slit. The distance between side walls 62 need not be constant, and can vary along either or both of the depth and/or length of the slit, as desired.

The function of the slit is two-fold. First, the slit weakens the inherent level of bending resistance which is associated with the unslit diameter of the rod. Namely, the rod has an initially lesser resistance to bending than an unslit rod of the same diameter and material. The slits thus provide a level of flexural capability greater than the flexural capability inherent in the unslit rod. Meantime, the use of the larger diameter rod, rather than simply selecting a lesser diameter rod, maintains an overall foundational strength level in the rod which is greater than the overall strength of a thinner rod.

Second, the configuration of the slits limits the degree to which the rod can be bent at the lesser bending resistance. Namely, as the rod is progressively bent in a given direction, the bending of the rod brings the side walls of each slit, on the inside of the bend, toward each other. As the magnitude of the bend progressively increases, the outer ends 64 of the side walls of a given such slit, adjacent the outer surface of the rod, move progressively closer to each other until, at some point, the outer ends of the side walls come into contact, typically abutting contact, with each other.

Until the outer ends 64 come into contact with each other, the resistance to bending, of the rod, is largely a function of the unslit portions 60 of the rod. Such bending resistance is typically represented by a linear increase in degree of bending response as the transverse bending force is increased. When the magnitude of the bending response has brought the outer ends 64, or other portions, of the side walls together, any further increase in bending force is applied across the abutting surfaces of the side walls, whereby the next subsequent response to further bending force is a step increase in bending resistance to such transverse bending forces.

The magnitude of the initial bending resistance, e.g. before the side wails abut, can be controlled by, among other factors, the depth of the slit and/or the length of the slit relative to the outer surface of the rod, as well as the effective cross-section of the unslit portion 60 of the rod. The amount of bend which must be actuated before the side walls abut, namely before the step increase in bending resistance becomes effective, can be controlled by, among other factors, the perpendicular distance between respective portions of the side walls of the affected slits.

Figure 17:
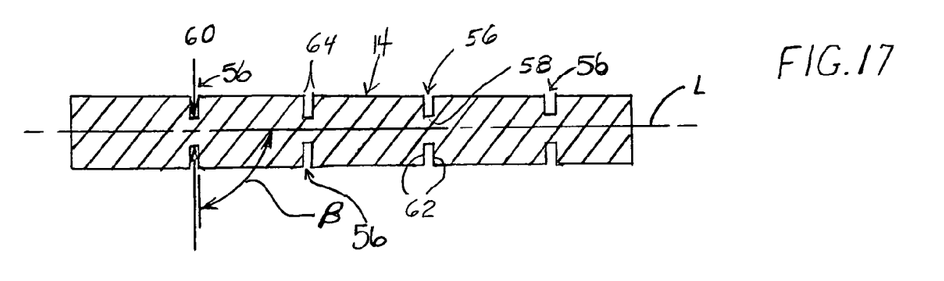
FIG. 17 shows a cross-section of the reinforcing rod as in FIG. 16, but wherein the slits are disposed at angles $\beta$, to the longitudinal axis, of 90 degrees.

FIGS. 15-16 illustrate an angle $\beta$ of about 25 degrees with respect to the longitudinal axis. FIG. 17 shows a similar embodiment, using slits wherein the angle $\beta$ is a perpendicular to the longitudinal axis.

FIG. 17 illustrates a cross-section similar to that of FIG. 16, in the same family of embodiments, wherein the slits, namely angles β, are perpendicular to the longitudinal axis.

The invention further contemplates that the angles β of the slits can be different for respective ones of the slits on a given rod. Further, considering the full array of slits on a given rod, the lengths, the widths, the depths, the distances between the side walls, the consistency of the widths, the consistency of the depths, the consistency of the distance between the side walls, the outline of the path traversed by the lengths of the slits, all can vary from slit to slit on a given rod. Thus, a wide array of patterns of slits, configurations of slits, on any given rod, are contemplated as being within the scope of the invention. The slits can be represented by an array of dead-end holes, or through holes, so long as the respective array of holes, whether dead end holes or through holes, provides the desired degree of flexibility, e.g. flex resistance, flexural response, to transverse bending forces exerted on the reinforcing rod.

Reinforcing rods 14, including cables 36, of the invention can employ, for example and without limitation, titanium compositions, titanium alloy compositions such as titanium-aluminum alloy compositions, or other titanium alloys, or stainless steel compositions. Other materials can be used in reinforcing rods 14 so long as such materials satisfy the safety and performance requirements required for reinforcing rods used in the human body environment, or animal body environment, as applies, and all such other materials are contemplated for the corresponding spinal support assemblies of this invention.

Any of the plastic materials known to be safe for use in living human or animal bodies, as applies, as implantable plastics, and which have suitable hardness and rigidity to satisfy the performance requirements of the spinal support assemblies described herein, can be employed for fabricating such reinforcing rods 14 as do not employ a stranded cable 36 as the primary flexure resistance structure. Such materials can, however, be employed, for example and without limitation, as cylindrical bodies which extend about such cables 36, and can be used as cables 36 where the cable applies primarily a tension reaction function as in FIGS. 2-7. Such implantable plastics can be used in fabricating rod elements 24, joint balls 26, end caps 30, and the various expressions of the cylindrical body, including in the embodiments of FIGS. 6-7. Where the plastic embodies sufficient tensile strength, the respective plastic materials can be used in or as cable 36 where the primary function of the cable is to apply a compressive force on the components of the rod assembly so as to apply compressive force between the respective ones of the rod assembly components. As with the metals, such materials must be both bio-stable and bio-compatible.

As such plastics, there can be mentioned, for example and without limitation, polyetherimide copolymer such as ULTEM®, acetal copolymer, polyethersulfone, also known as polyarylsulfone, such as RADEL A®, polyarylethersulfone such as RADEL R®, polycarbonate, ultra high molecular weight polyethylene, polyetheretherketone, also known as PEEK, available from Boedecker Plastics, Inc. Shiner, Texas, polyaryletherketone, also known as PEEK-OPTIMA®.

Such materials can be filled or unfilled, and can employ the usual additives and additive packages, including processing aids, so long as the resultant composition is suitable as an implantable plastic for use in a living, e.g. human or animal body.

While shown in transverse cross-section only in FIG. 9, reinforcing rods 14, and rod assemblies 25 typically have generally round cross-sections. Thus, cables 36 are generally round. Similarly, rod elements 24, joint balls 26, end caps 30, and cylindrical bodies 46, typically show round cross-sections when cut perpendicular to longitudinal axis "L". Other cross-sectional configurations are contemplated to the extent such configurations are consistent with the flexing and other functional features contemplated herein for the reinforcing rods and rod assemblies.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:

1. A spinal support assembly adapted to be used in a spinal fixation surgical procedure, said spinal support assembly having a first end and a second end, and comprising:
 a) at least first and second rod elements arranged in end-to-end relationship with each other, adjacent ones of said rod elements defining opposing ends thereof which face each other and cooperatively define one or more angularly-mobile joints therebetween, said ends of said rod elements having generally centrally-located apertures, such apertures being defined by circumferential edges of such apertures; and
 b) a cable extending from the first end of said spinal support assembly, through respective ones of the apertures in corresponding ones of said rod elements, to the second end of said spinal support assembly,
retraction forces in said cable drawing facing ones of the ends of said at least first and second rod elements, which define the one or more angularly-mobile joints, into frictional relationships with each other,
the apertures at the ends of said rod elements being generally sized to the size of said cable such that said cable interacts with the edges of the apertures at the ends of said rod elements and thereby generally prevents adjacent ends of adjacent said rod elements from moving transversely with respect to each other.

2. A spinal support assembly as in claim 1, said cable having knob-shaped enlargements at both the first and second ends thereof.

3. A spinal support assembly as in claim 2 wherein the retraction forces are maintained between said rod elements by tension in said cable.

4. A spinal support assembly as in claim 2 wherein a first end cap is positioned between said first rod element and said first knob-shaped enlargement and a second end cap is positioned between said second rod element and said second knob-shaped enlargement, wherein said first end cap has a first aperture extending therethrough and said second end cap has a second aperture extending therethrough, said first and second end caps being urged against said first and second rod elements by the tensile forces in said cable.

5. A spinal support assembly as in claim 1, said cable being pre-tensioned before any application of said spinal support assembly to any surgical procedure.

6. A spinal support assembly as in claim 5 wherein said cable extends through the first aperture formed through said first end cap and through the second aperture formed through said second end cap.

7. A spinal support assembly as in claim 1 wherein one of said rod elements has first and second female ends.

8. A spinal support assembly adapted to be used in a spinal fixation surgical procedure, said spinal support assembly having a first end and a second end, and comprising:
   a) at least first and second rod elements arranged in end-to-end relationship with each other, adjacent ones of said rod elements defining opposing ends thereof which face each other and cooperatively define one or more angularly-mobile joints therebetween, each of said ends of said rod elements having a generally centrally-located aperture; and
   b) a cable extending from the first end of said spinal support assembly, through respective ones of the apertures in corresponding ones of said rod elements, to the second end of said spinal support assembly,
retraction forces in said cable drawing facing ones of the ends of said at least first and second rod elements, which define the one or more angularly-mobile joints, into frictional relationships with each other,
said cable having knob-shaped enlargements at both the first and second ends thereof, said knob-shaped enlargements comprising welds
wherein a first end one of the apertures is located at the first end of said spinal support assembly, a second end one of the apertures is located at the second end of said spinal support assembly, a first one of said knob-shaped enlargements comprising a first enlarged end located outwardly of, and compressed against, the first end one of the apertures, and a second one of said knob-shaped enlargements comprising a second enlarged end located outwardly of, and compressed against, the second end one of the apertures.

9. A spinal support assembly adapted to be used in a spinal fixation surgical procedure, said spinal support assembly comprising:
   a) a flexible rod assembly having a first assembly end and a second assembly end, and comprising
      (i) at least first and second rod elements arranged in an end-to-end relationship with each other, adjacent ones of said rod elements defining opposing rod element ends which face each other and cooperatively define one or more angularly-mobile joints therebetween, such rod element ends having a generally centrally-located apertures, and
      (ii) a cable having first and second cable ends, said cable extending from the first end of said rod assembly, to the second end of said rod assembly, said cable being pre-tensioned prior to any application of said spinal support assembly to any surgical procedure such that retraction forces in said cable draw said rod elements into frictional relationships with each other.

10. A spinal support assembly as in claim 9 wherein respective adjacent ones of said rod elements are in direct frictional engagement with each other at the respective ends thereof, and wherein said adjacent ones of said rod elements are adapted to be articulated with respect to each other as accommodated by the respective frictional relationships, thereby accommodating limited and controlled motion of the treated portion of such patient's spine while stabilizing the treated portion of such patient's spine.

11. A spinal support assembly as in claim 9, said spinal support assembly further comprising a first end cap on the first assembly end and a second end cap on the second assembly end, said first and second end caps being urged against respective ones of said rod elements at the first and second assembly ends by the tensile forces in said cable.

12. A spinal support assembly as in claim 9, a first end one of the apertures being located at the first end of said flexible rod assembly, a second end one of the apertures being located at the second end of said flexible rod assembly, said cable having welds at the first and second ends thereof maintaining a tension on said cable, one of said welds comprising a first enlarged cable end located outwardly of, and compressed against, the first end one of the apertures, and a second one of said welds comprising a second enlarged cable end located outwardly of, and compressed against, the second end one of the apertures.

13. A spinal support assembly as in claim 9 wherein a first end cap is positioned adjacent said first rod element and a second end cap is positioned adjacent said second rod element, a first aperture extending through said first end cap and a second aperture extending through said second end cap, said cable extending through the first aperture in said first end cap and through the second aperture in said second end cap, said first and second end caps being urged against the respective said first and second rod elements by tensile forces in said cable.

14. A spinal support assembly as in claim 9, a given said rod element having a side wall, first and second end walls of said given rod element extending across a cross-section of said given rod element, thereby closing off the ends of the given said rod element and defining an internal cavity, having a cavity length between said first and second end walls, said cable extending through the internal cavity without touching said side wall.

15. A spinal support assembly as in claim 9 wherein said rod elements are drawn toward each other by said cable, whereby compressive forces are maintained between said respective rod elements in said spinal support assembly.

16. A spinal support assembly as in claim 9 wherein said cable is made of material selected from the group consisting of titanium, titanium alloy, and stainless steel.

17. A spinal support assembly adapted to be used in a spinal fixation surgical procedure, said spinal support assembly comprising:
   a) a rod structure having a first rod structure end and a second rod structure end, said rod structure including a plurality of rod elements each having first and second rod element ends, a first such end of one of said rod elements facing a second such end of an adjacent one of said rod elements, and apertures defining a path through said rod structure between the first and second rod structure;
   b) a cable extending from the first end of said rod structure, along the path and through said rod structure, including through respective ones of the apertures, to the second end of said rod structure, said cable drawing facing ones of the ends of said rod elements into frictional relationships with each other,
   the apertures in said rod structure being sized and configured to the size of said cable such that said cable interacts with edges of the apertures at the ends of said rod elements and thereby generally prevents adjacent ends of adjacent said rod elements from moving transversely with respect to each other; and c) an attachment adapter assembly configured to attach said rod structure to first and second support vertebrae of a such patient's spine.

18. A spinal support assembly as in claim 17 wherein a first one of the apertures is located at the first end of said rod structure, a second one of the apertures is located at the second end of said rod structure, said cable including a first enlarged end of said cable, said first enlarged end being located outwardly of, and compressed against, the aperture located at the first end of said rod structure, and a second opposing enlarged end of said cable being located outwardly of, and compressed against, the aperture located at the second end of said rod structure.

19. A spinal support assembly as in claim 18 wherein the first and second enlarged ends are welds.

20. A spinal support assembly as in claim 17, a given said rod element having a side wall, first and second end walls of said given rod element extending across a cross-section of said given rod element, thereby closing off the ends of the given said rod element and defining an internal cavity, having a cavity length between said first and second end walls, said cable extending through the internal cavity without touching said side wall.

21. A spinal support assembly as in claim 17 wherein said cable is pre-tensioned before any application of said spinal support assembly to any surgical procedure, retraction forces in said cable effectuating the drawing of facing ones of said rod elements into engaging relationship with each other, whereby compressive forces are transferred directly between said respective rod elements in said spinal support assembly.

22. A spinal support assembly as in claim 17 wherein at least one of said cable and one of said rod elements is made of material selected from the group consisting of titanium, titanium alloy, stainless steel, polyetherimide copolymer, acetal copolymer, polyethersulfone, polycarbonate, ultra high molecular weight polyethylene, polyetheretherketone, and polyaryletherketone.

23. A spinal support assembly as in claim 17, said cable being pre-tensioned before any application of said spinal support assembly to any surgical procedure.

24. A spinal support assembly adapted to be used in a spinal fixation surgical procedure, said spinal support assembly comprising:
a) a rod structure having a first rod structure end and a second rod structure end, said rod structure including a plurality of rod elements having male and female ends, a said male end of at least one said rod element facing a said female end of an adjacent said rod element, a plurality of apertures in said rod structure defining a path through said rod structure between the first and second rod structure ends; and
b) a cable extending from the first end of said rod structure, along the path and through said rod structure, including through respective ones of the apertures, to the second end of said rod structure, said cable being pre-tensioned prior to any application of said spinal assembly in any such spinal fixation surgical procedure, retraction forces in said cable forcing facing ones of said rod elements into frictional relationships with each other,
the apertures in said rod structure being sized and configured to the size of said cable such that said cable interacts with edges of the apertures at the ends of the rod elements and thereby generally prevents adjacent ends of adjacent said rod elements from moving transversely with respect to each other.

25. A spinal support assembly as in claim 24 wherein a first end one of the apertures is located at the first end of said rod structure, a second end one of the apertures is located at the second end of said rod structure, said pre-tensioned cable including a first enlarged end of said cable located outwardly of, and compressed against, the first end aperture located at the first end of said rod structure, and a second opposing enlarged end of said cable located outwardly of, and compressed against, the second end aperture located at the second end of said rod structure.

26. A spinal support assembly as in claim 24, further comprising an attachment adapter assembly configured to receive said rod structure therethrough, including receiving at least one said rod element thereinto, thereby to attach said rod assembly to a first support vertebra of a patient's spine.

27. A spinal support assembly as in claim 24, a given said rod element having a side wall, end walls of said given rod element closing off the ends of the given said rod element and defining an internal cavity, having a cavity length between said end walls, said cable passing through the cavity and being spaced apart from said side wall along the entirety of the length of the internal cavity.

28. A spinal support assembly as in claim 24 wherein said rod elements are forced toward each other by said pre-tensioned cable, whereby compressive forces are maintained between said respective rod elements in said spinal support assembly.

29. A spinal support assembly as in claim 24 wherein at least one of said pre-tensioned cable and said rod elements is made of material selected from the group consisting of titanium, titanium alloy, stainless steel, polyetherimide copolymer, acetal copolymer, polyethersulfone, polycarbonate, ultra high molecular weight polyethylene, polyetheretherketone, and polyaryletherketone.

30. A spinal support assembly as in claim 24, said spinal support assembly further comprising a first end cap on the first assembly end and a second end cap on the second assembly end, said first and second end caps being urged against end ones of said rod elements at the first and second assembly ends by the tensile forces in said cable.

31. A spinal support assembly as in claim 30, each of said first and second end caps having an aperture extending therethrough.

32. A spinal support assembly as in claim 30 wherein each of said end caps is integral with said rod structure.

33. A spinal support assembly, comprising:
a) a rod structure having a first rod structure end and a second rod structure end, and comprising at least first and second substantially enclosed rod elements arranged in end-to-end relationship with each other, a given said rod element having a side wall and end walls which in combination define a generally enclosed internal cavity, said end walls of adjacent ones of said rod elements having cooperating configurations which accommodate angular articulation of said rod elements with respect to each other;
b) apertures formed through said end walls of said rod elements defining a path through said rod structure between the first and second rod structure ends, including through said at least first and second rod elements, such apertures being defined at said end walls by circumferential edges of such apertures;
c) a cable extending from the first end of said rod structure along the path and through said at least first and second rod elements, including through respective ones of the apertures, to the second end of said rod structure, said cable holding the ends of respective adjacent ones of said at least first and second rod elements in frictional relationships with each other, said cable being pre-tensioned before any application of said spinal support assembly to any surgical procedure, and maintaining the tension such that said pre-tensioned cable applies a stress on said rod structure, the apertures in said rod elements being sized and configured to the size of said cable such that said cable interacts with edges of the apertures at the ends of said rod elements and thereby generally prevents ends of adjacent ones of said rod elements from moving transversely with respect to each other; and d) an attachment adapter assembly adapted and configured to receive said rod structure, including receiving at least one said rod element thereinto, thereby to attach said rod structure to a first vertebra of a body, said stressed rod structure, in combination with said pre-tensioned cable, accommodating limited angular motion of said first rod structure end relative to said second rod structure end, the frictional relationships between said rod elements accommodating limited angular motion of rod elements between the first and second ends of said rod structure, while limiting such angular movement, whereby the frictional relationships of said rod elements accommodate limited angular movement of a treated portion of a patient's spine while said spinal support assembly provides a required level of stabilization to such treated portion of such patient's spine.

34. A spinal support assembly as in claim 33 wherein said rod elements are drawn toward each other by the retraction forces in said cable, whereby compressive forces are maintained between engaging ones of said rod elements in said spinal support assembly.

35. A spinal support assembly as in claim 34 wherein at least one of said cable and said rod elements is made of a material selected from the group consisting of titanium, titanium alloy, stainless steel, polyetherimide copolymer, acetal copolymer, polyethersulfone, polycarbonate, ultra high molecular weight polyethylene, polyetheretherketone, and polyaryletherketone.

* * * * *